United States Patent
Nagaoka et al.

(10) Patent No.: US 9,492,821 B2
(45) Date of Patent: Nov. 15, 2016

(54) LIQUID FEEDER AND CHEMICAL ANALYZER INCLUDING SAME

(71) Applicant: Hitachi High-Technologies Corporation, Tokyo (JP)

(72) Inventors: Yoshihiro Nagaoka, Tokyo (JP); Hisao Inami, Tokyo (JP); Motohiro Yamazaki, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/770,978

(22) PCT Filed: Jan. 30, 2014

(86) PCT No.: PCT/JP2014/052089
§ 371 (c)(1),
(2) Date: Aug. 27, 2015

(87) PCT Pub. No.: WO2014/148117
PCT Pub. Date: Sep. 25, 2014

(65) Prior Publication Data
US 2016/0016167 A1    Jan. 21, 2016

(30) Foreign Application Priority Data
Mar. 19, 2013  (JP) ................................ 2013-057128

(51) Int. Cl.
*B01L 3/00* (2006.01)
*B01F 3/00* (2006.01)
(Continued)

(52) U.S. Cl.
CPC ...... *B01L 3/502715* (2013.01); *B01F 13/0083* (2013.01); *B01J 19/00* (2013.01);
(Continued)

(58) Field of Classification Search
CPC ................... B01L 3/502715; B01L 3/502738; B01L 3/5027; B01L 3/502; B01L 3/50;
(Continued)

(56) References Cited

U.S. PATENT DOCUMENTS

2004/0151629 A1 * 8/2004 Pease .................... B01L 3/5027
422/68.1
2009/0126516 A1 * 5/2009 Yamamoto .......... B01F 13/0071
73/864.22

FOREIGN PATENT DOCUMENTS

| JP | 2004-521315 A | 7/2004 | |
| JP | 2006-023209 A * | 1/2006 | ............. G01N 30/32 |
| WO | 02/07884 A2 | 1/2002 | |

OTHER PUBLICATIONS

Tamaki, English Machine Translation of JP 2006-023209 A of Description and Claims, obtained on Dec. 29, 2015.*
(Continued)

*Primary Examiner* — Christine T Mui
(74) *Attorney, Agent, or Firm* — Mattingly & Malur, PC (57) ABSTRACT

In some examples, a liquid feeding device includes a main flow passage in which a fluid may be fed between an upstream side and a downstream side. A first flow passage may branch from the main flow passage, and may include a narrow flow passage at a terminal end portion, having a smaller cross-sectional area than the first flow passage. A liquid feeding mechanism may feed the fluid to the main flow passage and the first flow passage. The narrow flow passage may suppress the fluid from leaking from first flow passage. Thus, the liquid feeding device may quantitatively determine a first volume of the fluid by filling the first flow passage with the fluid, and subsequently feeding the quantitatively determined fluid back to the main flow passage.

19 Claims, 9 Drawing Sheets

(51) Int. Cl.
  *B01J 19/00* (2006.01)
  *B01F 13/00* (2006.01)
(52) U.S. Cl.
  CPC .. *B01L 3/502738* (2013.01); *B01L 2200/0621* (2013.01); *B01L 2300/0867* (2013.01); *B01L 2300/0877* (2013.01); *B01L 2400/0633* (2013.01)
(58) Field of Classification Search
  CPC ............... B01L 3/00; B01L 2200/0621; B01L 2200/06; B01L 2200/00; B01L 2300/0867; B01L 2300/0861; B01L 2300/08; B01L 2400/06; B01L 2400/0633; B01L 2400/00; B01F 13/0083; B01F 13/0074; B01F 13/0059
  USPC .................................... 422/502, 501, 500, 50
  See application file for complete search history.

(56) References Cited

OTHER PUBLICATIONS

English Translation of International Search Report of PCT/JP2014/052089. Mar. 2014, pp. 1-7, obtained on Dec. 29, 2015.*

\* cited by examiner

LIQUID FEEDER AND CHEMICAL ANALYZER INCLUDING SAME

TECHNICAL FIELD

Invention relates to a liquid feeding device (a liquid feeder) for making a liquid flow, and a chemical analysis apparatus (a chemical analyzer) using the same.

BACKGROUND ART

PTL 1 discloses a technique relating to a liquid feeding device in the related art. PTL 1 discloses that microdroplets are metered into defined volumes and are subsequently incorporated into a variety of biological assays. In PTL 1, a device is disclosed which splits a nonoliter-volume liquid sample and move it using external air, and has a plurality of hydrophobic regions. That is, a liquid placed at an inlet is drawn in by using surface forces, and the front of the liquid moves by a gas-intake pathway that is in fluidic communication with the channel, and moves to the liquid-abutting hydrophobic region. Next, PTL 1 discloses a system in which gas from a gas source is ejected from the gas-intake pathway to split a microdroplet with a predetermined volume between electronic components are fabricated on the same substrate material, allowing sensors and controlling circuitry to be incorporated in the same device.

CITATION LIST

Patent Literature

PTL 1: JP-T-2004-521315

SUMMARY OF INVENTION

Technical Problem

However, in the system disclosed in PTL 1, the position of the front of a liquid is defined by preventing a liquid from entering a hydrophobic region using hydrophobicity. However, there is a possibility that a liquid cannot be stopped immediately before the above-described region depending on the physical properties of a liquid specimen in a case where, for example, the surface tension between the specimen and the surface of the hydrophobic region is small.

The present invention has been made in consideration of the above circumstances, and an object of the present invention is to provide a liquid feeding device which can accurately quantitatively determine an arbitrary liquid and can feed the arbitrary liquid.

Solution to Problem

In order to solve the above-described problem, a liquid feeding device of the present invention has the following characteristics.

(1) A liquid feeding device according to an aspect of the invention includes a branched portion at which a fluid is branched into a main flow passage that feeds the fluid from an upstream side to a downstream side and a first branched flow passage that is branched from the main flow passage; a narrow flow passage which is provided at a terminal end portion, which is different from the branched portion of the first branched flow passage, and has a cross-sectional area smaller than that of the first branched flow passage; and a liquid feeding mechanism which feeds the fluid to the main flow passage and the first branched flow passage, in which the narrow flow passage suppresses the fluid, which is fed from the main flow passage side to the first branched flow passage using the liquid feeding mechanism in the branched portion, from leaking from first branched flow passage, quantitatively determines fluid as a first volume by filling the first branched flow passage, which has the first volume, with the fluid, and feeds the quantitatively determined fluid to the main flow passage.

(2) A liquid feeding device according to another aspect of the invention includes a first branched portion at which a fluid is branched into a main flow passage that feeds the fluid from an upstream side to a downstream side and a first branched flow passage that is branched from the main flow passage; a confluence flow passage joining the main flow passage further on an upstream side than the first branched portion; a confluence portion of the confluence flow passage and the main flow passage; a second branched portion which is provided further on an upstream side than the confluence portion and is branched from the main flow passage into a second branched flow passage; and a liquid feeding mechanism which feeds the fluid to the main flow passage, the confluence flow passage, and the first and the second branched flow passages, in which a first fluid is fed to the main flow passage until the first fluid having a first volume reaches the first branched portion from the main flow passage further on an upstream side than the second branched portion, and in which a second fluid is made to flow into the main flow passage from the confluence portion by feeding the second fluid to the confluence flow passage, the first fluid from the second branched portion to the confluence portion is fed to the second branched flow passage from the second branched portion due to the flow of the second fluid to the main flow passage, the second fluid is made to flow into the main flow passage from the confluence portion by feeding the second fluid to the confluence flow passage, and the first fluid from the confluence portion to the first branched portion is fed to the main flow passage on an downstream side of the first branched portion due to the flow of the second fluid to the main flow passage.

In addition, a chemical analysis apparatus of the present invention is constituted using the liquid feeding device of the above-described (1) or the liquid feeding device of the above-described (2).

Advantageous Effects of Invention

According to the present invention, it is possible to provide the liquid feeding device which can accurately quantitatively determine an arbitrary liquid and can feed the arbitrary liquid.

DESCRIPTION OF EMBODIMENT

Hereinafter, an embodiment of the present invention will be described with reference to the drawings.

Figure 1:
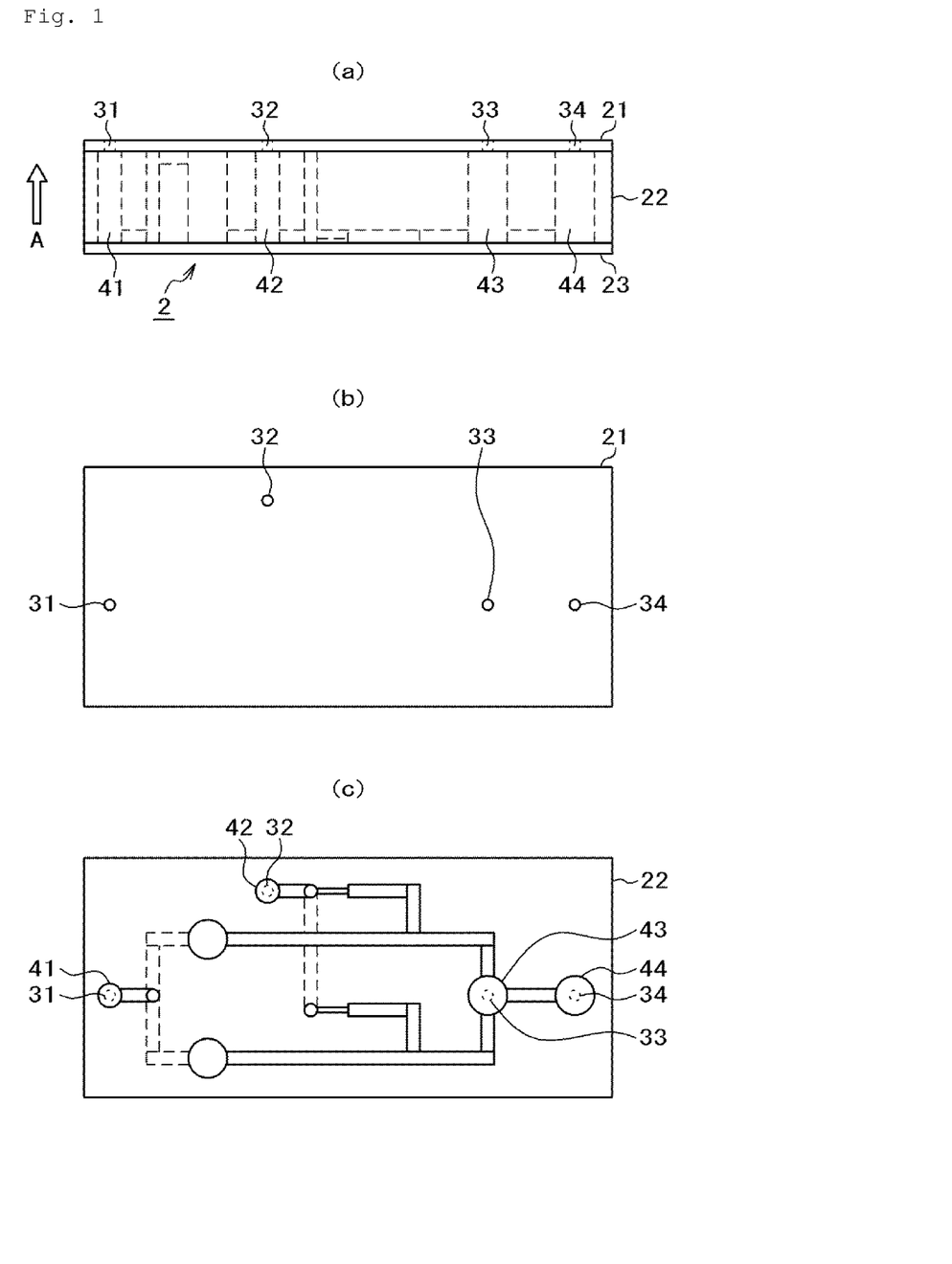
FIG. 1 is a detailed view of a liquid feeding device.
Figure 2:
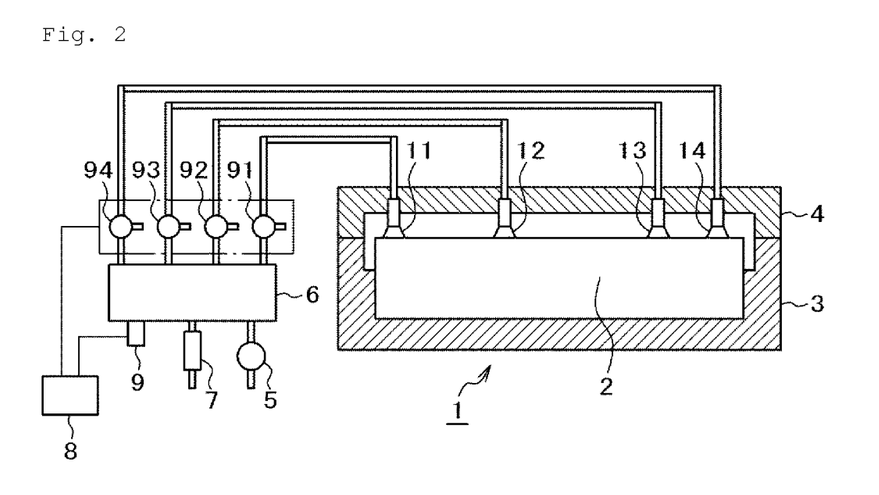
FIG. 2 is a configuration view of a specimen treatment apparatus.

FIG. 1 is a detailed view illustrating a liquid feeding device of the present invention. FIG. 2 shows a configuration view of a specimen treatment apparatus using the liquid feeding device.

First, the configuration of the specimen treatment apparatus shown in FIG. 2 will be described. A specimen treatment apparatus 1 is constituted of a device mounting portion 3 in which a liquid feeding device 2 is mounted, and an upper lid 4 which holds the liquid feeding device 2 and seals the specimen treatment apparatus 1.

An air outlet/inlet port to be described later is provided on the upper surface of the liquid feeding device 2, and connection portions 11, 12, 13, and 14 for air are provided on the upper lid 4 in order to make air flow in and out the entrance.

When the specimen treatment apparatus 1 is sealed by mounting the liquid feeding device 2 in the device mounting portion 3 and bringing the upper lid 4 into close contact with the device mounting portion 3, the connection portions 11, 12, 13, and 14 for air are brought into close contact with respective air outlet/inlet ports on the upper surface of the liquid feeding device 2, and therefore, it is possible to guide high pressure air into the liquid feeding device.

High pressure air generated by a pump 5 is held by an air chamber 6 and is regulated to an almost constant pressure using a regulator 7. The air regulated to a constant pressure in the air chamber 6 is connected to the connection portions 11, 12, 13, and 14 for air by pipes through valves 91, 92, 93, and 94, respectively.

The valves 91, 92, 93, and 94 are controlled by a controller 8, and it is selected whether air is supplied from the air chamber 6 to the connection portions 11, 12, 13, and 14 for air; air is released to the atmosphere from the connection portions 11, 12, 13, and 14 for air; or air is fully closed.

In addition, a pressure sensor 9 which measures pressure within the air chamber 6 is provided in the liquid feeding device as necessary, and the controller 8 controls the valves 91, 92, 93, and 94 in accordance with a signal of the pressure sensor 9.

Example 1

The details of the liquid feeding device 2 are shown in FIG. 1. FIG. 1(a) shows a side view of the liquid feeding device 2.

As shown in the side view, the liquid feeding device 2 is constituted of a flow portion 22 in which flow passages or containers are formed; a top plate 21 which is joined to the upper side of the flow portion 22; and a bottom plate 23 which is joined to the lower surface.

The top plate 21 has a plurality of air outlet/inlet ports (31, 32, 33, and 34 in this drawing). In FIG. 1(a), containers (41, 42, 43, and 44) or the air outlet/inlet ports, or a flow passage which connects the containers are formed inside the liquid feeding device 2, and therefore, are shown by a broken line.

FIG. 1(b) shows a plan view (in an arrow A direction from the inside of the flow portion 22) when the top plate 21 is viewed from the lower surface side. The air outlet/inlet ports 31, 32, 33, and 34 are provided at a position at which the connection portions 11, 12, 13, and 14 for air shown in FIG. 2 are brought into close contact with the top plate 21. Accordingly, air is introduced into the air outlet/inlet ports 31, 32, 33, and 34 from the connection portions 11, 12, 13, and 14 for air through the valves 91, 92, 93, and 94.

FIG. 1(c) shows a plan view (in an arrow A direction from the inside of, the flow portion 22) when the flow portion 22 is viewed from the lower surface side. This drawing is a view when the flow portion 22 is viewed from the arrow A direction in a state where the bottom plate 23 is removed. Therefore, flow passages provided on the bottom plate 23 side are shown by a solid line and flow passages provided inside or on the top plate 21 are shown by a broken line. The containers 41, 42, 43, and 44 are provided so as to penetrate through the flow portion 22 as shown in FIG. 1(a). In addition, the air outlet/inlet ports 31, 32, 33, and 34 are arranged at positions respectively corresponding to the containers 41, 42, 43, and 44.

<<Description of Mixing Operation>>

An operation of mixing two liquids using the liquid feeding device 2 will be described while referring to FIG. 3.

Figure 3A:
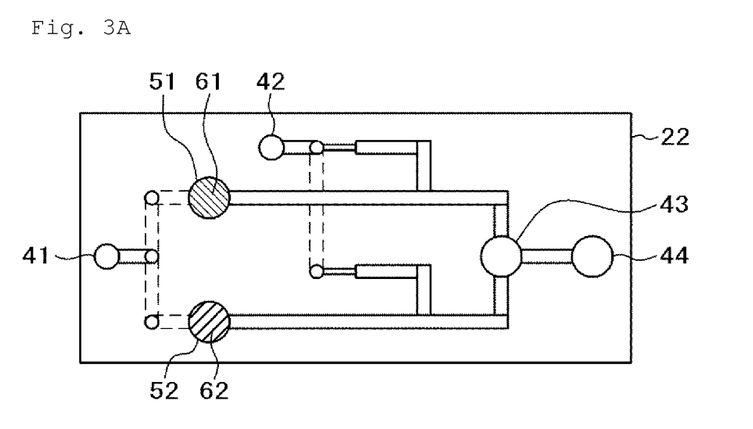
FIG. 3A is a view illustrating an operation of mixing two liquids using the liquid feeding device.
Figure 3B:
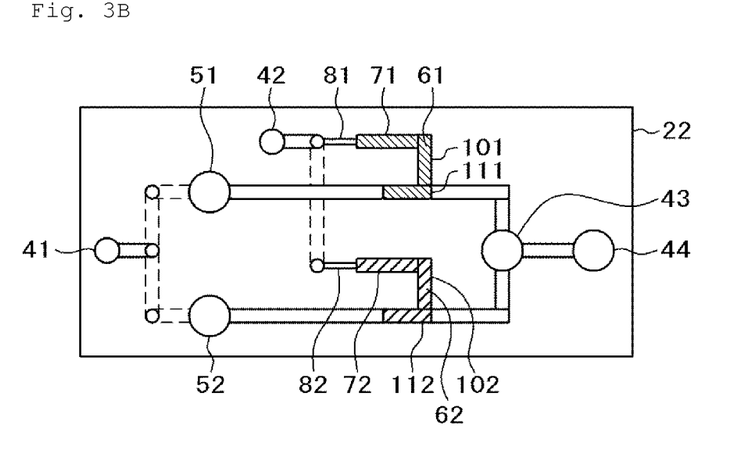
FIG. 3B is a view illustrating an operation of mixing two liquids using the liquid feeding device.
Figure 3C:
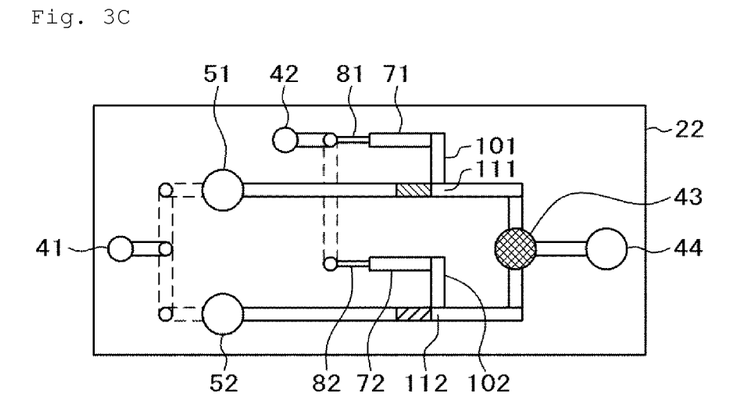
FIG. 3C is a view illustrating an operation of mixing two liquids using the liquid feeding device.

FIG. 3 is a view corresponding to FIG. 1(c) and is a plan view when the flow portion 22 is viewed from the lower surface side.

FIG. 3A shows an initial state in which a liquid 61 and a liquid 62 are respectively injected into a container 51 and a container 52 in advance, and other containers (41, 42, 43, and 44) or other flow passages are filled with air. The valves 91, 92, 93, and 94 (refer to FIG. 2) are in a fully closed state.

FIG. 3B shows a state where the liquid 61 and the liquid 62 are made to flow into flow passages 71 and 72.

First, the liquid 61 and the liquid 62 are made to flow into the flow passages 71 and 72 by making the flow portion be in a state where air is released to the atmosphere from the connection portion 12 for air by opening the valve 92 while setting the flow portion to be in a state where air is supplied from the air chamber 6 to the connection portion 11 for air by opening the valve 91. That is, high pressure air in the air chamber 6 flows into the container 41 from the connection portion 11 for air, and the liquids 61 and 62 in the containers 51 and 52 are extruded by high pressure air and flow into the flow passages 71 and 72 through flow passages 101 and 102. The containers 51 and 52 are connected through a flow passage (shown by a dotted line in the drawing), and therefore, air pressure is applied to the containers. The flow passage 71 or 72 is filled with the liquid 61 or 62 which then starts to slightly flow into a narrow flow passage 81 or 82. The narrow flow passages 81 and 82 are connected through a flow passage (shown by a dotted line in the drawing).

At the time when the liquids 61 and 62 start to flow into the narrow flow passages 81 and 82, the states of the valves 91 and 92 are switched to fully closed states to stop the flow of the liquids 61 and 62.

The timing at which the states of the valves 91 and 92 are switched to be in a fully closed state may be predetermined or may be based on a signal of the pressure sensor 9 which is attached to the air chamber 6.

For example, in a case where the switching timing is previously determined, time required for a liquid, which has the largest viscosity between liquids that are considered as the liquids 61 and 62, to reach the narrow flow passages 81 and 82 from the containers 51 and 52 may be obtained through pre-experiments or pre-calculation.

Particularly, in the present example, with the use of the narrow flow passages 81 and 82 with a small cross-sectional area, it is possible to prevent the valves 91 and 92 from being switched to be in a fully closed state before the liquid 61 or 62 reaches the narrow flow passage 81 or 82. The reason will be described below.

The narrow flow passages 81 and 82 are designed to have small cross-sectional area compared to other flow passages such as the flow passages 71 and 72 or the flow passages 101 and 102, and the flow resistance thereof becomes large. Furthermore, in a state where the pressure of the air chamber 6 is controlled by the regulator 7 to be almost constant, the flow rate of the liquid 61 or 62 becomes smaller after the liquid 61 or 62 flows into the narrow flow passage 81 or 82 compared to that before the liquid 61 or 62 flows into the narrow flow passage 81 or 82. Accordingly, if the cross-sectional area of the narrow flow passages 81 and 82 is made extremely narrower, e.g. one tenth than the cross-sectional area of other flow passages such as flow passages 71 and 72, even if the valves are switched at a timing with more sufficient allowance than the predetermined switching timing, the flow rate the liquids flowing into the narrow flow passages 81 and 82 is low. Therefore, it is possible to ignore the liquid amount flowing into the narrow flow passages 81 and 82 compared to the liquid amount held by the flow passages 71 and 72. The cross-sectional area of the narrow flow passages 81 and 82 is set to one tenth in the present example, but may be determined in accordance with the accuracy of quantitative determination performed by the liquid feeding device.

In addition, the liquids 61 and 62 flow by being pressurized by high pressure air flowing into the container 41 which is a common driving source, and in general, the resistance of the flow passage through which the liquid 61 flows from the container 51 to the narrow flow passage 81 and the resistance of the flow passage through which the liquid 62 flows from the container 52 to the narrow flow passage 82 are designed so as to be the same as each other. However, in a case where the flow resistances become different from each other due to a problem such as a machining error, for example, in a case where the flow resistance of the flow passage through which the liquid 61 flows is large, the liquid 62 first flows into a narrow flow passage. Even in this case, the flow rate of the liquid 62 decreases since the flow resistance of the liquid 62 rapidly becomes large at the time when the liquid 62 starts to flow into the narrow flow passage 82 and the flow rate of the liquid 61 which has not reached the narrow flow passage 81. Therefore, it is possible to ignore the difference in the liquid amount flowing into the narrow flow passages 81 and 82 compared to the liquid amount held by the quantitative determination flow passages 71 and 72.

The reason for which it is possible to ignore the difference in the liquid amount flowing into the narrow flow passages 81 and 82 will be described below using a pipeline network flow analysis result in FIG. 6.

Figure 6:
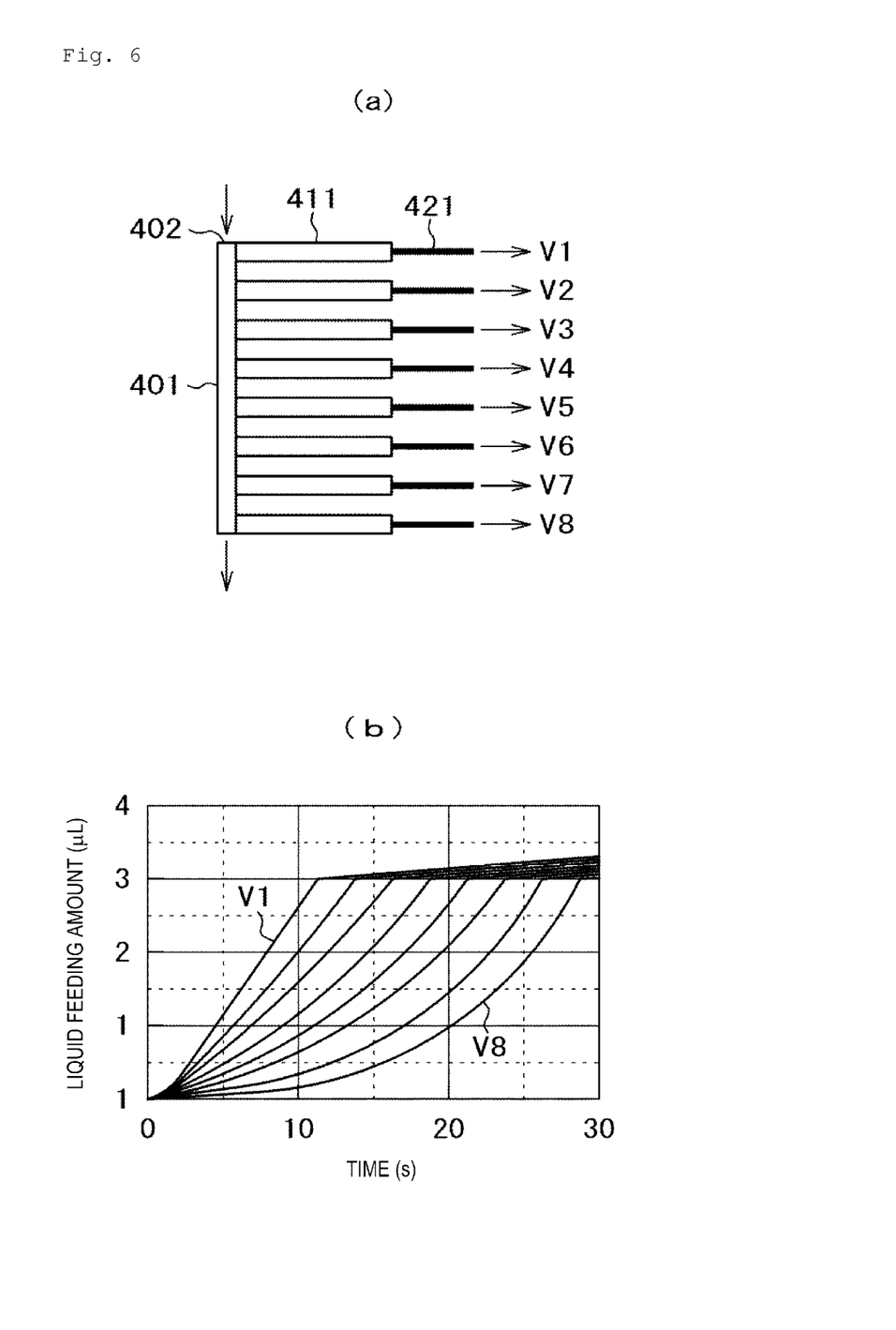
FIG. 6 is a view illustrating an effect of a narrow flow passage.

FIG. 6(a) shows a flow passage structure in which a fluid flows into a flow passage 401 through an inflow port 402 and flows by being divided into eight flow passages 411. The downstream sides of the eight flow passages are constituted by narrow flow passages 421 with a small cross-sectional area. When the liquid amount (cumulative volume of the fluid flowing into the flow passages 411) of feeding the fluid to each of the flow passages 411 is set to V1, V2, . . . , and V8 from a side close to the inflow port 402, the time change in each liquid feeding amount is as shown in FIG. 6(b).

FIG. 6(b) is a pipeline network flow analysis result of the time change in the liquid feeding amounts when water is supplied to the inflow port 402 at 1.4 µL/s, in which the flow passage 401 has an inner diameter of 0.5 mm and a length of 70 mm, the flow passages 411 each are branched from the flow passage 401 at even intervals and have an inner diameter of 0.5 mm and a length of about 16 mm (the volume of a flow passage is set to 3 µL), and the narrow flow passage 421 has an inner diameter of 0.1 mm and a length of 12 mm. Accordingly, FIG. 6(b) is data when the ratio of the cross-sectional area of the flow passage 411 to the cross-sectional area of the narrow flow passage 421 is set to 1/25.

In FIG. 6(b), the liquid feeding amounts V1 to V8 are sequentially illustrated from the left to the right of the drawing, and the notation of V2 to V7 is omitted.

As shown in FIG. 6(b), the liquid feeding amount V1 from the flow passage closest to the inflow port 402 most rapidly becomes large and the liquid feeding amount V8 from the flow passage farthest from the inflow port 402 most slowly increases. This is because the flow resistance of the flow passage 401 from the inflow port 402 to a branched portion of each of the flow passages 411 becomes larger and a liquid is made more difficult to flow as the position of the branched portion is farther from the inflow port. However, when the liquid feeding amount reaches 3 µL, water flows into the narrow flow passage 421 and the flow resistance rapidly increases. Therefore, the increase in the liquid feeding amount in the flow passage is small. As a result, there is no particular change in the volume of other flow passages from 3 µL until the last liquid feeding amount V8 reaches 3 µL. In the result of FIG. 6(b), V1 is 3.294 µL and it is possible to suppress the increase in the liquid feeding amount to about 10% of V8 (=3 µL). This analysis has been obtained using an inner diameter and a length of a flow passage in which the variation in the liquid feeding amount becomes within 10%. Moreover, it is possible to determine the structures of the flow passages such that the liquid feeding amounts of the flow passages vary so as to be predetermined liquid feeding amounts by using the narrow flow passage.

The case where the timing at which the valves are switched is determined in advance has been described above, but the valves 91 and 92 may be switched to be in a fully closed state using a signal of the pressure sensor 9 shown in FIG. 2. That is, in FIGS. 3A and 3B, the pressure of the air chamber 6 shown in FIG. 2 temporarily steeply increases since the flow resistance of the liquids 61 and 62 rapidly becomes large at the time when the liquids 61 and 62 reach the narrow flow passages 81 and 82. At this timing, the valves 91 and 92 may be switched. The pressure of the air chamber 6 temporarily steeply increases every time when the time at which the liquid 61 reaches the narrow flow passage 81 and the time at which the liquid 62 reaches the narrow flow passage 82 are different from each other, and therefore, the valves 91 and 92 may be switched every time.

Next, in FIG. 3C, the liquid 61 and the liquid 62 are set to be in a state of flowing into the container 43 by making the valve 92 be in a state where air is supplied from the air chamber 6 to the connection portion 12 for air and making the valve 93 be in a state of being released to the atmosphere from the connection portion 13 for air. That is, high pressure air in the air chamber 6 flows into container 42 from the connection portion 12 for air, and the liquid 61 in the narrow flow passage 81, flow passages 71 and 101, and the branched portion 111 flow into the container 43. Similarly, the liquid 62 in the narrow flow passage 82, flow passages 72 and 102, and the branched portion 112 flows into the container 43. The valves 92 and 93 are switched to be in a fully closed state at the time at which the liquids 61 and 62 flow into the container 43. The switching timing may be predetermined or may be based on a signal of the pressure sensor 9 which is attached to the air chamber 6.

In the system in which the switching timing is predetermined, the total amount of the liquids 61 and 62 may flow into the container 43, and therefore, a sufficiently long period of time may elapse for the flowing. In the system in which a signal of the pressure sensor 9 is used at a switching timing, when the total amount of the liquids 61 and 62 flows into the container 43, the flow resistance decreases and the pressure of the air chamber 6 temporarily rapidly decreases. Therefore, the valves may be switched at that timing.

If the total volume of the flow passages 71 and 101 and the branched portion 111 is set so as to be the same as the liquid amount of the liquid 61 which is required for mixing the liquids 61 and 62 and the total volume of the flow passages 72 and 102 and the branched portion 112 is set so as to be the same as the liquid amount of the liquid 62 which is required for mixing the liquids 61 and 62, the amount of the liquids 61 and 62 flowing into the container 43 becomes larger by the amount of liquids flowing into the narrow flow passages 81 and 82 than the necessary amount which is required for mixing the liquids. However, with the use of the above-described narrow flow passages 81 and 82 which have a small cross-sectional area, it is possible to ignore the liquid amount flowing into the narrow flow passages 81 and 82 compared to the liquid amount held by the flow passages 71 and 72.

Here, the above-described total volume will be described in detail while referring to FIG. 3B.

Actually, the flow passages 71 and 101 and the branched portion 111 have no partition therebetween, and are continuously connected to each other. The flow passage 71 in FIG. 3B is represented by a rectangular shape so as to recognize the volume of this flow passage for the convenience of description. Similarly, the flow passage 101 is also represented by a rectangular shape and the branched portion 111 is also represented by the rectangular shape. Accordingly, the total volume of the flow passages 71 and 101 and the branched portion 111 is obtained by adding the volume of the illustrated rectangular regions. However, the volume of the branched portion 111 is a volume of a common region in which a region extending from the flow passage 101 and a main flow passage intersect with each other.

In addition, the range in which an extra amount of a flowing liquid can be ignored, that is, the variation in the liquid feeding amount can be appropriately set. In present example, the cross-sectional area of the narrow flow passages 81 and 82 is set to one tenth of the cross-sectional area of the flow passages 71 and 72 or the like as described above, and the inner diameter and the length of a flow passage are set such that the variation in the liquid feeding amount at that time becomes within 10%.

Accordingly, in a case where the variation in the liquid feeding amount is set to a smaller value, the structure of a flow passage may be determined such that the ratio of the cross-sectional area of a flow passage and the cross section of a narrow flow passage becomes a predetermined variation in the liquid feeding amount.

After the liquids 61 and 62 flow into the container 43, the liquids in the container 43 are made to flow into the container 44 by making the valve 93 be in a state where air is supplied from the air chamber 6 to the connection portion 13 for air and making the valve 94 be in a state of being released to the atmosphere from the connection portion 14 for air. Furthermore, the liquids in the container 44 are made to flow into the container 43 by making the valve 94 be in a state where air is supplied from the air chamber 6 to the connection portion 14 for air and making the valve 93 be in a state of being released to the atmosphere from the connection portion 13 for air. By repeating such operations, the liquids 61 and 62 are mixed by making the liquids repeatedly flow between the containers 43 and 44.

The timing at which the valves are switched for the above-described repetitive flow may be after the flow of the total amount of the liquids is completed, similarly to the above description. However, the valves may be switched in a short period of time before the flow is completed since it is possible to mix the liquids by only making part of the liquids flow.

Finally, the operation is completed after the mixed liquid is held by the container 44 and all of the valves are fully closed.

In the present example, the total volume of the flow passages 71 and 101 and the branched portion 111 is set so as to be the same as the liquid amount of the liquid 61 which is required for mixing the liquids 61 and 62 and the total volume of the flow passages 72 and 102 and the branched portion 112 is set so as to be the same as the liquid amount of the liquid which is required for mixing the liquids 61 and 62. Therefore, it is possible to guide the two liquids with a predetermined amount to the container 43 and mix the liquids, by providing the narrow flow passages 81 and 82.

As described above, according to the present invention, as shown in the present Example 1, it is possible to accurately quantitatively determine each of liquids to be mixed, by providing narrow flow passages. Furthermore, the accuracy of the quantitative determination can be set by setting the ratio of the cross-sectional area of a flow passage to the cross-sectional area of a narrow flow passage.

Example 2

Figure 4A:
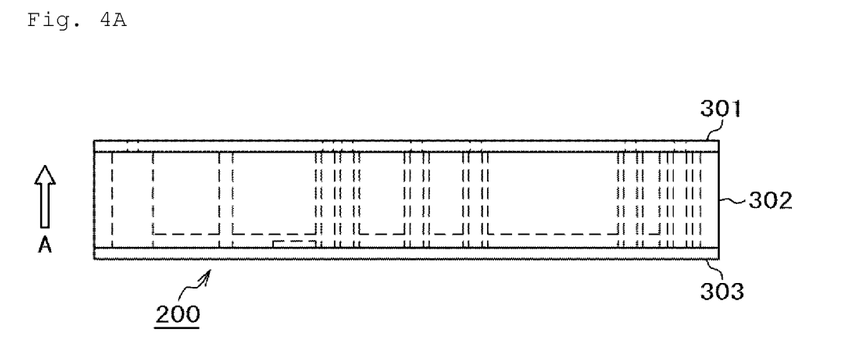
FIG. 4A is a detailed view of the other example of a liquid feeding device.
Figure 4B:
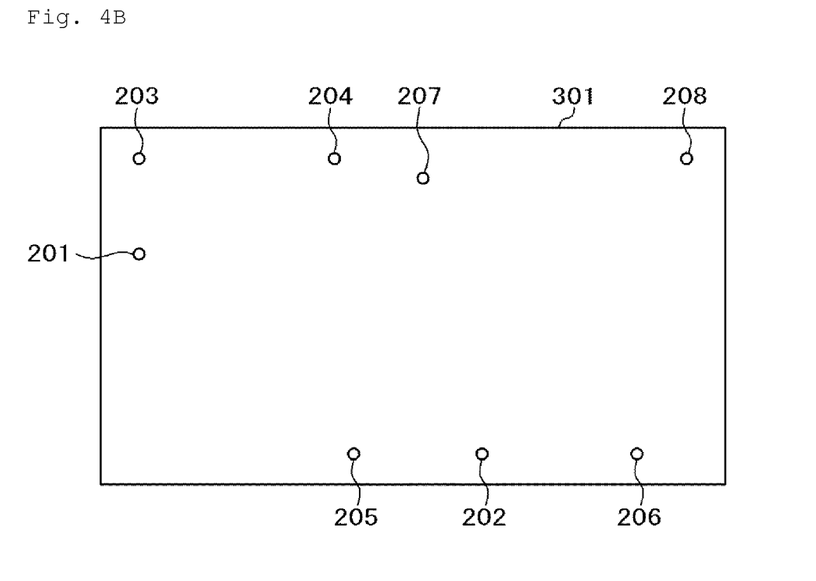
FIG. 4B is a detailed view of the other example of the liquid feeding device.
Figure 4C:
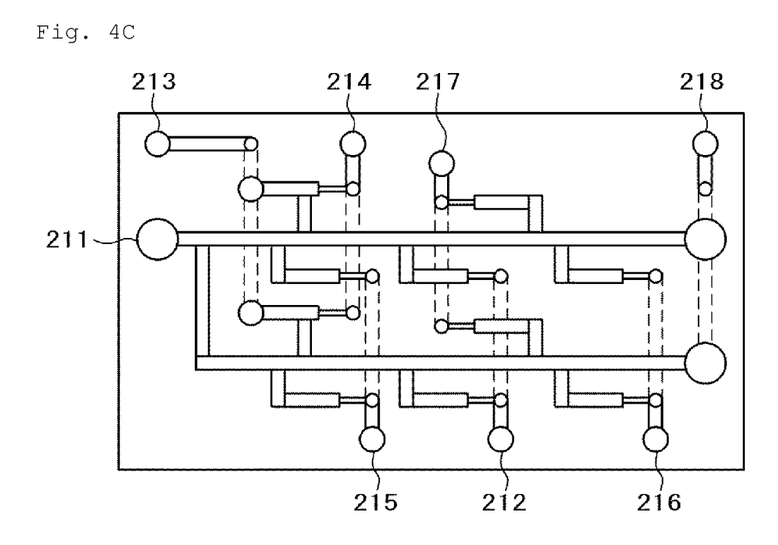
FIG. 4C is a detailed view of the other example of the liquid feeding device.

FIGS. 4A to 4C show another example of the present invention. The method of feeding and quantitatively determining a fluid in the present example is the same as that in Example 1. However, the present example is different from Example 1 in that the present example has a configuration of feeding or quantitatively determining liquids such that air before and after two liquids in a flow passage which are fed when mixing the two liquids or air between both of the fluids is not mixed in.

FIG. 4A is a side view of a liquid feeding device 200. Similarly to the liquid feeding device 2 in FIG. 1, a top plate 301 which has a plurality of vent holes is joined to the upper surface of a flow portion 302, in which flow passages or containers are formed, a bottom plate 303 is joined to the lower surface of the flow portion 302.

FIG. 4B is a plan view (in an arrow A direction from the inside of the flow portion 302) when the top plate 301 is viewed from the lower surface side. FIG. 4C is a plan view (in an arrow A direction from the inside of the flow portion 302) when the flow portion 302 is viewed from the lower surface side. Most of flow passages are formed on the lower surface side and only flow passages with a broken line are formed on the upper surface side. This drawing shows a view when the flow portion 302 is viewed from the arrow A direction in a state where the bottom plate 303 is removed. Therefore, flow passages provided on the bottom plate 303 side are shown by a solid line and flow passages provided inside or on the top plate 301 side are shown by a broken line.

In addition, similarly to the liquid feeding device 2 in FIG. 1, a connection portion (not shown in the drawing) for air the same as that shown in FIG. 2 is constituted so as to be brought into close contact with each of air outlet/inlet ports 201, 202, 203, 204, 205, 206, 207, and 208 shown in FIG. 4B, and it is selected whether air is supplied from the air chamber to the connection portions for air; air is released to the atmosphere from the connection portions for air; or air is fully closed, by switching the corresponding valves.

In addition, in the flow portion 302, containers 211, 212, 213, 214, 215, 216, 217, and 218 are provided at positions corresponding to the air outlet/inlet ports 201, 202, 203, 204, 205, 206, 207, and 208 of the top plate 301 so as to penetrate the flow portion 302.

<<Description of Operation of Mixing Two Liquids>>

An operation of dividing and mixing two liquids using the liquid feeding device 200 will be described while referring to FIGS. 2, 4A to 4C, and 5A to 5F.

Figure 5A:
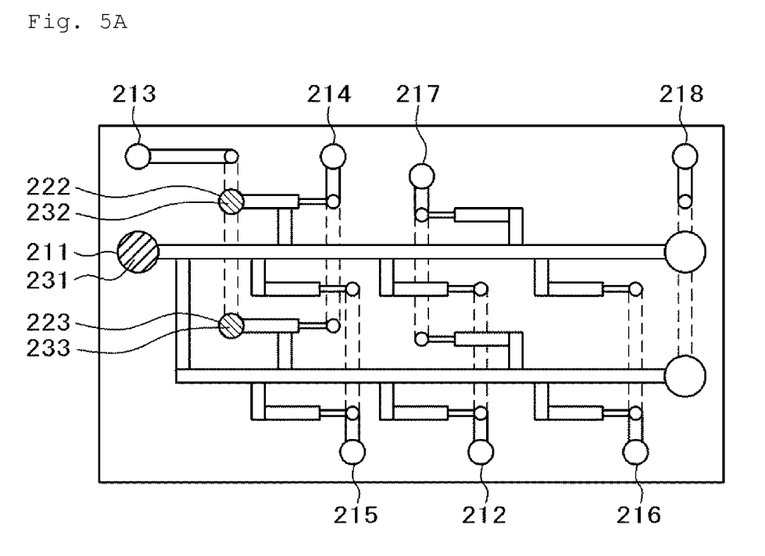
FIG. 5A is a view illustrating an operation of mixing two liquids using the liquid feeding device.

FIG. 5A shows an initial state in which a liquid 231, a liquid 232, and a liquid 233 are respectively injected into a container 211, a container 222, and a container 223 in advance, and other containers or the flow passage are filled with air. Valves which are provided in the middle of pipes connected from the air chamber to the air outlet/inlet ports 201, 202, 203, 204, 205, 206, 207, and 208 are in a fully closed state.

Figure 5B:
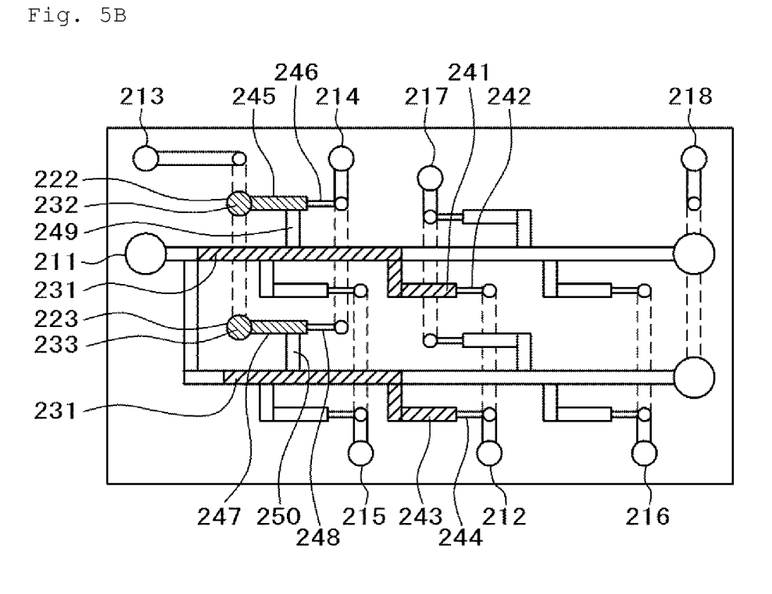
FIG. 5B is a view illustrating an operation of mixing two liquids using the liquid feeding device.

FIG. 5B shows a state in which the liquids 231, 232, and 233 are made to flow into flow passages 241, 243, 245, and 247 by making the flow portion be in a state where air is supplied from the air chamber to the connection portions 201 and 203 for air and making the flow portion be in a state of being released to the atmosphere from the connection portion 202 and 204 for air, by switching four valves. That is, high pressure air in the air chamber flows into the containers 211 and 213 from the connection portions 201 and 203 for air.

The air flowing which has flowed into the container 213 extrudes the liquids 232 and 233 in the containers 222 and 223 and makes the liquids flow into the flow passages 245 and 247. The flow passages 245 and 247 are filled with the liquids 232 and 233 which then start to slightly flow into narrow flow passages 246 and 248.

In contrast, the air which has flowed into the container 211 extrudes the liquid 231 in the container 211 and makes the liquid flow into the flow passages 241 and 243 by dividing the liquid into two flow passages. The flow passages 241 and 243 are filled with the liquid 231 which then starts to slightly flow into narrow flow passages 242 and 244.

At the time when the liquid 231 has flowed into the narrow flow passages 242 and 244 and liquids 232 and 233 have respectively flowed into the narrow flow passages 246 and 248, the states of the valves are switched to fully closed states to stop the flow of the liquids 231, 232, and 233.

Figure 5C:
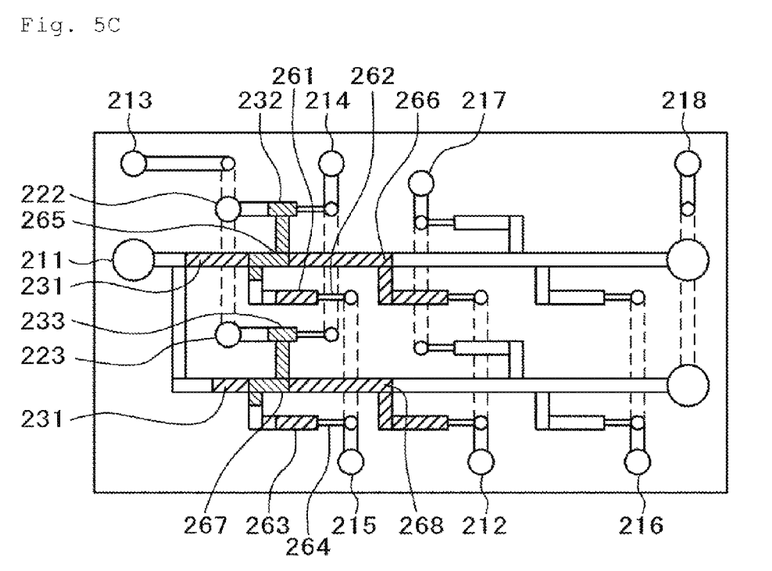
FIG. 5C is a view illustrating an operation of mixing two liquids using the liquid feeding device.

Next, in FIG. 5C, the flow portion is made to be in a state where air is supplied from the air chamber to the connection portion 203 for air and in a state of being released to the atmosphere from the connection portion 205 for air, by switching two valves. Accordingly, the flow portion is made to be in a state where the liquids 232 and 233 are made to flow into flow passages 261 and 263 and part of air and the liquid 231 within confluence flow passages 249 and 250 in FIG. 5B is discharged into the flow passages 261 and 263. That is, high pressure air within the air chamber flows into the container 213 from the connection portion 203 for air; the liquid 231, air, and the liquid 232 sequentially flow into the flow passage 261; and the liquid 231, air, and the liquid 233 sequentially flow into the flow passage 263. At the time when the liquid 231 has flowed into the narrow flow passages 262 and 264, the states of the valves are switched to fully closed states to stop the flow of the liquids 231, 232, and 233.

Here, the confluence flow passage 249 shown in FIG. 5B is filled with air. It can be seen that the air is fed to the flow passage 261 as shown in FIG. 5C and there is no region for air in the liquid 231. Air in the confluence flow passage 250 also undergoes similar treatment.

Figure 5D:
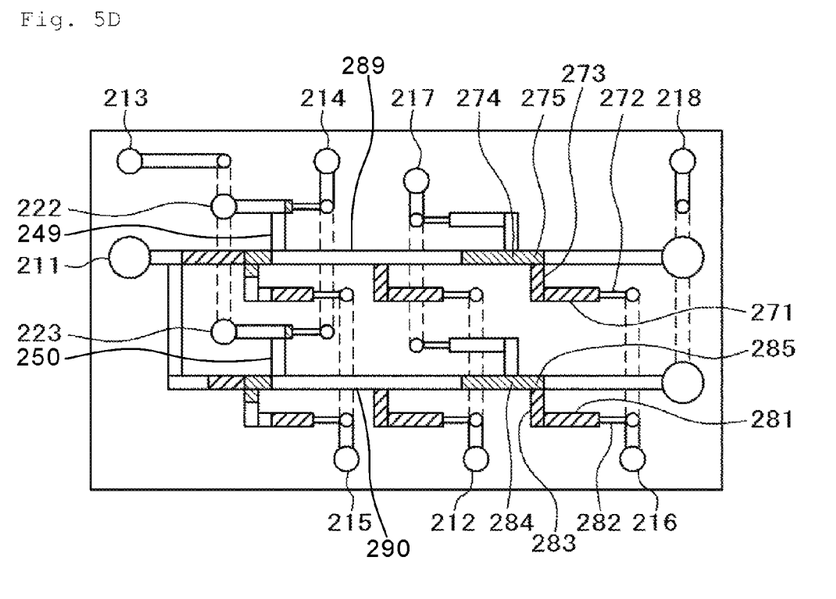
FIG. 5D is a view illustrating an operation of mixing two liquids using the liquid feeding device.

Next, in FIG. 5D, the flow portion is made to be in a state where air is supplied from the air chamber to the connection portion 203 for air and in a state of being released to the atmosphere from the connection portion 206 for air, by switching two valves. Accordingly, the flow portion is made to be in a state where the liquids 231 and 232 are made to flow into a flow passage 271 side and the liquids 231 and 233 are made to flow into a flow passage 281 side. That is, high pressure air within the air chamber flows into the container 213 from the connection portion 203 for air to make the liquid 231 within a main flow passage 289 from a confluence portion 265 to a branched portion 266 in FIG. 5C, and the liquid 232 within the confluence flow passage 249 on the upstream side, flow into the flow passage 271 side; and make the liquid 231 within a main flow passage 290 from a confluence portion 267 to a branched portion 268 in FIG. 5C, and the liquid 233 within the confluence flow passage 250 on the upstream side, flow into the flow passage 281 side. At the time when the liquid 231 starts to flow into the narrow flow passages 272 and 282, the states of the valves are switched to fully closed states to stop the flow of the liquids 231, 232, and 233.

Figure 5E:
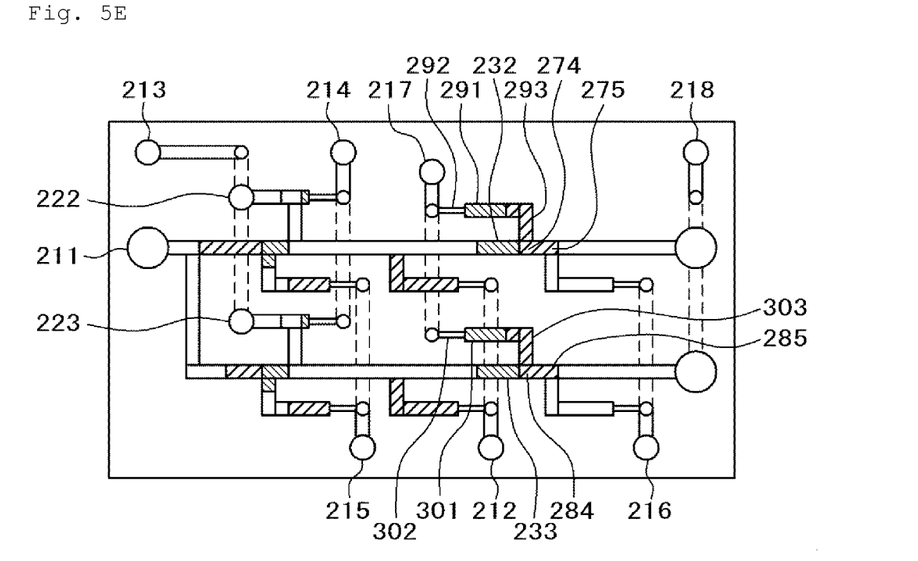
FIG. 5E is a view illustrating an operation of mixing two liquids using the liquid feeding device.

Next, in FIG. 5E, the flow portion is made to be in a state where air is supplied from the air chamber to the connection portion 206 for air and in a state of being released to the atmosphere from the connection portion 207 for air, by switching two valves. Accordingly, the flow portion is made to be in a state where the liquids 231 and 232 are made to flow into the flow passage 291 side and the liquids 231 and 233 are made to flow into a flow passage 301 side. That is, high pressure air within the air chamber flows into the container 216 from the connection portion 206 for air to make liquids within a flow passage from a branched portion 274 to a branched portion 275 and within a flow passage 273 and the flow passage 271, in FIG. 5D to flow into the flow passage 291 side and liquids within a flow passage from a branched portion 284 to a branched portion 285 and within a flow passage 283 and the flow passage 281, in FIG. 5D to flow into the flow passage 301 side. At the time when the liquids start to flow into narrow flow passages 292 and 302, the states of the valves are switched to fully closed states to stop the flow of the liquids.

The operation in FIG. 5E is an operation for mixing two liquids of liquids 231 and 232 and two liquids of liquids 231 and 233 which are mixed by performing the following operation. That is, liquids are made to flow into the flow passages 271 and 281 side by making the flow portion be in a state where air is supplied from the air chamber to the connection portion 207 for air and in a state of being released to the atmosphere from the connection portion 206 for air, by switching two valves. The two liquids of liquids 231 and 232 and the two liquids of liquids 231 and 233 are mixed by repeating flow from the flow passages 271 and 281 to the flow passages 291 and 301 and reverse flow thereof.

Figure 5F:
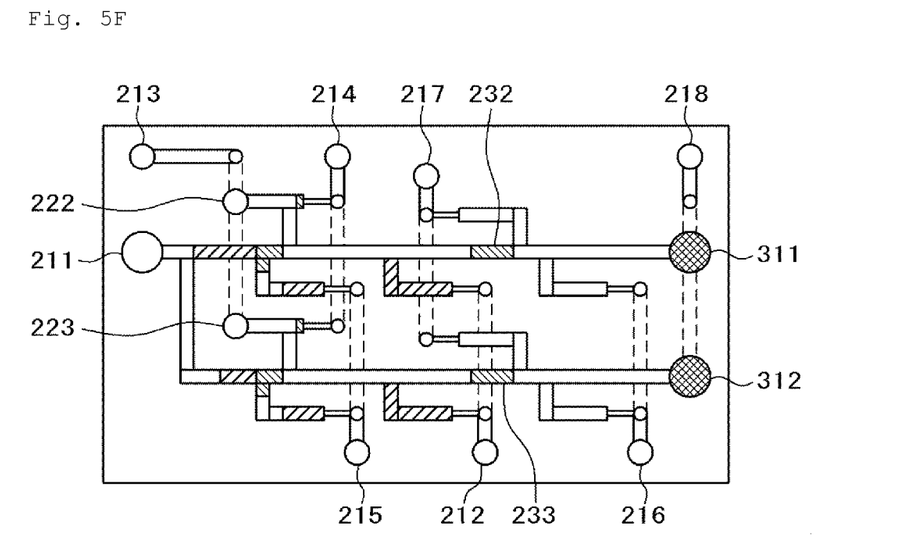
FIG. 5F is a view illustrating an operation of mixing two liquids using the liquid feeding device.

Finally, as shown in FIG. 5F, the mixed liquids are made to flow into containers 311 and 312 by making the flow portion be in a state where air is supplied from the air chamber to the connection portion 207 or 206 for air and in a state of being released to the atmosphere from the connection portion 208 for air, by switching two valves.

In Example 1 (refer to FIGS. 2 and 3A to 3C), a device of mixing and quantitatively determining two liquids has been described in which when two liquids flow into the container 43, air first flows thereinto, and then, the liquids flow thereinto. For this reason, there is a possibility that air bubbles may be mixed into the container 43.

In contrast, in Example 2 (FIGS. 4A to 4C and FIGS. 5A to 5F), the point that air bubbles are not mixed in when mixing two liquids is regarded as an advantage, and air bubbles are prevented from being mixed in through the operation in FIG. 5C. That is, air (within the flow passage 249 or 250 in FIG. 5B) between two liquids (liquids 231 and 232 or liquids 231 and 233) to be mixed is extruded to the flow passage 261 or 263 side by the liquid 232 or 233 together with the liquid 231; the liquids 231 and 232 come into contact with each other at the confluence portion 265; and the liquids 231 and 233 come into contact with each other at the confluence portion 267, so as to prevent air bubbles from being mixed in.

At this time, the role of the narrow flow passages 262 and 264 is to prevent liquids from unnecessarily flowing into the flow passages 261 and 263. The liquid 231 is made difficult to flow into the narrow flow passages 262 and 264 after the flow passages 261 and 263 are filled with the liquid 231. An object of the operation shown in FIG. 5C is to prevent air bubbles from being mixed in by discharging air within the confluence flow passage 249 or 250 in FIG. 5B as described above; bringing the liquids 231 and 232 into contact with each other at the confluence portion 265; and bringing the liquids 231 and 233 into contact with each other at the confluence portion 267. Therefore, air may be discharged to the flow passages 261 and 263 side from the confluence portions 265 and 267. If the liquids 232 and 233 are made to flow excessively, the liquids 232 and 233 are wasted. Accordingly, if the device is designed to have a volume for discharging air at the time when the flow passages 261 and 263 are filled with the liquid 231, an effective structure may be obtained in which the liquid is prevented from flowing excessively using the narrow flow passages 262 and 264.

Particularly, the liquids 232 and 233 are extruded by high pressure air flowing into the container 213, and therefore, there is a possibility that the flow rates of both of the liquids may be different from each other. For this reason, there is a possibility that the time for which the flow passage 261 is filled with a liquid and the time for which the flow passage 263 is filled with a liquid may be different from each other. However, the difference in the liquid feeding amount is small since the flow rate of a liquid on a flow passage side which is first filled with the liquid becomes small using the narrow flow passage.

In FIG. 5C, the boundary position of two liquids (liquids 231 and 232 or liquids 231 and 233) to be mixed is determined, by the liquids 232 and 233 entering the confluence portions 265 and 267. The liquid 231 within a flow passage from the confluence portion 265 to the branched portion 266 and a flow passage from the confluence portion 267 to branched portion 268 flow to the downstream side in the next FIG. 5D and is stirred in the next step. Therefore, the liquid 231 is quantitatively determined through the above-described operation of determining the boundary position.

In FIG. 5D, the total amount of the two liquids to be mixed is quantitatively determined. That is, the liquids to be stirred in FIG. 5E after FIG. 5D are liquids in a flow passage from the branched portion 274 to branched portion 275 and in the flow passages 273 and 271, and are liquids in a flow passage from the branched portion 284 to branched portion 285 and in flow passages 283 and 281. The liquid 231 is quantitatively determined in the previous step (FIG. 5C), and therefore, the fact that the amount of liquids to be stirred is quantitatively determined means that the liquids 232 and 233 are quantitatively determined. That is, the two liquids to be mixed are quantitatively determined in the steps up to FIG. 5D.

Accordingly, in the operation in FIG. 5D, it is desirable that the liquids are prevented from flowing after the flow passages 271 and 281 are filled with the liquids. To do this, the narrow flow passages 272 and 282 are provided to increase the flow resistance, thereby making the liquids difficult to flow.

In the stirring operation after FIG. 5E, it is unnecessary for the flow passages 291 and 301 or flow passages 271 and 281 to be filled with the liquids, and part of the liquids to be mixed may flow into the flow passages.

Alternately, the total volume of the flow passages 291 and 293 and the total volume of the flow passages 301 and 303 are made to be larger than the volume of each mixed liquid; the total amount of the mixed liquid is made to flow to the flow passages 291 and 301; a valve connected to the container 217 is fully closed and a valve connected to the container 213 is opened; the liquids 232 and 233 which remain immediately before the branched portions 274 and 284 are moved to the upstream side, that is, to the container 213 side by communicating a valve connected to the container 216 with the air chamber as it is. Accordingly, the liquids under mixing and the liquids 232 and 233 may be prevented from being mixed in.

A first object of the operation in FIG. 5B is to determine the leading position (branched portions 266 and 268 in FIG. 5C) for quantitatively determining each liquid by dividing the flow of the liquid 231 into two flow passage. In contrast, the flow of the liquids 232 and 233 is not always necessary due to an operation of discharging air and is a prior operation for discharging air in FIG. 5C.

The present example relates to a device of preparing two types of mixed liquids (mixed liquid of liquids 231 and 232 and mixed liquid of liquids 231 and 233). The liquid 231 has been divided into two flow passages, but may be divided into multiple flow passages in order to prepare three or more kinds of mixed liquids. Variation in flow resistance of flow passages occurs as the number of flow passages is increased. However, with the use of a narrow flow passage, the flow resistance increases if a predetermined amount or more of a liquid flows. Therefore, the flow rate of the flow passages is uniformed, thereby enabling quantification.

As described above, the present Example 2 has an effect of suppressing air from being mixed into a mixed liquid when mixing a plurality of liquids, in addition to the effect shown in Example 1. As a result, it is possible to more accurately quantitatively determine liquids to be mixed.

REFERENCE SIGNS LIST 1 specimen treatment apparatus,
2 liquid feeding device, 3 device mounting portion,
4 upper lid,
5 pump,
6 air chamber,
7 regulator,
8 controller,
9 pressure sensor,
11, 12, 13, 14 connection portion for air,
21 top plate,
22 flow portion,
23 bottom plate,
31, 32, 33, 34 air outlet/inlet port,
41, 42, 43, 44 container,
51, 52 container,
71, 72 flow passage,
81, 82 narrow flow passage,
91, 92, 93, 94 valve,
101, 102 flow passage,
111, 112 branched portion,
200 liquid feeding device,
201, 202, 203, 204, 205, 206, 207, 208 air outlet/inlet port,
211, 212, 213, 214, 215, 216, 217, 218 container,
241, 243, 245, 247, 249, 250, 261, 263, 271, 273, 281, 283,291,
301 flow passage,
242, 244, 246, 248, 262, 264, 272, 282, 292, 302 narrow flow passage,
265, 267 confluence portion,
266, 268, 274, 275, 284, 285 branched portion
301 top plate,
302 flow portion,
303 bottom plate,
401 flow passage,
402 inflow port
411 flow passage,
421 narrow flow passage.

The invention claimed is:

1. A liquid feeding device comprising:
a main flow passage able to feed a fluid between an upstream side and a downstream side;
a branched portion including a first branched flow passage that is branched from the main flow passage;
a narrow flow passage which is provided at a terminal end portion of the first branched flow passage, which is different from the branched portion of the first branched flow passage, and has a cross-sectional area smaller than that of the first branched flow passage; and
a liquid feeding mechanism which is configured to:
feed the fluid to the main flow passage and the first branched flow passage, wherein the narrow flow passage suppresses the fluid from leaking from the first branched flow passage,
quantitatively determine the fluid as a first volume by filling the first branched flow passage, which has the first volume, with the fluid, and
feed the quantitatively determined fluid in the first branched flow passage and a first portion of fluid in the main flow passage at the branched portion through the main passage to a container, which is downstream of the first branched portion, while a second portion of the fluid in the main flow passage remains in the main flow passage adjacent to the branched portion.

2. The liquid feeding device according to claim 1, wherein a first fluid with a second volume which is inserted into the upstream side of the main flow passage is fed to the first branched flow passage through the branched portion using the liquid feeding mechanism,
wherein a portion of the second volume of the first fluid, with which the first branched flow passage is filled, is quantitatively determined so as to become the first volume, by filling the first flow passage, which has a volume less than the second volume, and
wherein the first fluid which is quantitatively determined as the first volume using the liquid feeding mechanism is fed to the main flow passage through the branched portion.

3. The liquid feeding device according to claim 1, comprising:
a plurality of the main flow passages,
wherein a first fluid, which is inserted into one upstream side of the plurality of main flow passages, and a second fluid, which is inserted into another upstream side of the plurality of main flow passages, are quantitatively determined, and
wherein the container is a mixing container and the quantitatively determined first fluid and second fluid are fed to the mixing container by the liquid feeding mechanism for mixing.

4. A liquid feeding device comprising:
a main flow passage able to feed a fluid between an upstream side and a downstream side;
a first branched portion at which a first branched flow passage is branched from the main flow passage;
a confluence flow passage joining the main flow passage on an upstream side of the first branched portion at a confluence portion of the confluence flow passage and the main flow passage;
a second branched portion disposed on an upstream side of the confluence portion and branched from the main flow passage into a second branched flow passage; and
a liquid feeding mechanism configured to feed the fluid to the main flow passage, the confluence flow passage, and the first and the second branched flow passages,
wherein the liquid feeding mechanism is configured to:
feed a first fluid to the main flow passage until the first fluid, having a first volume, reaches the first branched portion on a downstream side of the second branched portion, and
cause a second fluid to flow into the main flow passage at the confluence portion by feeding the second fluid to the confluence flow passage, wherein:
the first fluid located between the second branched portion and the confluence portion is fed to the second branched flow passage due to the flow of the second fluid to the main flow passage, and
the first fluid located between the confluence portion and the first branched portion is fed to the main flow passage on a downstream side of the first branched portion due to the flow of the second fluid to the main flow passage.

5. The liquid feeding device according to claim 4, further comprising:
a first narrow flow passage which is provided on a downstream side of the first branched flow passage and has a cross-sectional area smaller than that of the first branched flow passage; and
a second narrow flow passage which is provided on a downstream side of the second branched flow passage and has a cross-sectional area smaller than that of the second branched flow passage;
wherein a leaked amount of the fluids, with which the first and the second branched flow passages are filled, from the flow passages, is controlled by the first and the second narrow flow passages, respectively.

6. The liquid feeding device according to claim 4, further comprising:
a third branched portion disposed on a downstream side of the first branched portion and branched from the main flow passage into a third branched flow passage; and
a fourth branched portion disposed on a downstream side of the third branched portion and branched from the main flow passage into a fourth branched flow passage;
wherein, the liquid feeding mechanism is configured to feed the fluid to the main flow passage, the confluence flow passage, and the first to the fourth branched flow passages, wherein:
the second fluid is made to flow into the main flow passage at the confluence portion by feeding the second fluid to the confluence flow passage,
the first fluid located in the main flow passage on a downstream side of the confluence portion is fed to the main flow passage and the fourth branched flow passage due to the flow of the second fluid to the main flow passage, and
the second fluid and the first fluid located in the main flow passage from the third branched portion to the fourth branched portion are fed to the third branched flow passage.

7. The liquid feeding device according to claim 6, further comprising:
a first narrow flow passage which is provided on a downstream side of the first branched flow passage and has a cross-sectional area smaller than that of the first branched flow passage;
a second narrow flow passage which is provided on a downstream side of the second branched flow passage and has a cross-sectional area smaller than that of the second branched flow passage;
a third narrow flow passage which is provided on a downstream side of the third branched flow passage and has a cross-sectional area smaller than that of the third branched flow passage; and
a fourth narrow flow passage which is provided on a downstream side of the fourth branched flow passage and has a cross-sectional area smaller than that of the fourth branched flow passage,
wherein a leaked amount of the fluids, with which the first to the fourth branched flow passages are filled, from the flow passages, is controlled by the first to the fourth narrow flow passages, respectively.

8. The liquid feeding device according to claim 1, wherein the liquid feeding mechanism has a control valve, which feeds the fluid by introducing or discharging air through opening and closing operations, on an upstream side and a downstream side of the main flow passage and on a downstream side of the narrow flow passage, and
wherein air is introduced from the upstream side and air pressure is applied to the fluid by opening the control valve on the upstream side and the downstream side of the main flow passage, and the fluid is fed by selectively discharging air from at least one of the downstream side of the main flow passage or the downstream side of the narrow flow passage.

9. The liquid feeding device according to claim 1, wherein the liquid feeding mechanism makes the fluid flow into one or more of the branched flow passages by opening a control valve which is attached to a downstream side of the narrow flow passage, and the fluid is discharged from the branched flow passages by switching the control valve which is attached to the downstream side of the narrow flow passage.

10. A chemical analysis apparatus which has the liquid feeding device according to claim 1.

11. The liquid feeding device according to claim 1, wherein:
the liquid feeding mechanism has a control valve to feed the fluid by introducing or discharging air through opening and closing operations on at least one of the upstream side or the downstream side, and
the liquid feeding mechanism is configured to close the control valve based at least in part on at least one of:
passage of a predetermined amount of time since opening the control valve; or
a change in the air pressure exceeding a threshold.

12. The liquid feeding device according to claim 11, wherein the liquid feeding mechanism comprises a pressure sensor to send a signal to indicate that the change in the air pressure exceeds the threshold.

13. The liquid feeding device according to claim 3, wherein:
the mixing container is a first mixing container, the liquid feeding device further comprising a second mixing container connected to the first mixing container by the mixing passage, and
the liquid feeding mechanism is configured to move mixed fluid between the first mixing container and the second mixing container for mixing the first and second fluids.

14. The liquid feeding device according to claim 3, further comprising:
a first fluid container connected to a first main flow passage;
a second fluid container connected to a second main flow passage; and
a single gas inlet connected to the first fluid container and the second fluid container, the single gas inlet connected to the liquid feeding device for feeding the first fluid from the first fluid container to the first main flow passage, and for feeding the second fluid from the second fluid container to the second main flow passage.

15. The liquid feeding device according to claim 4, wherein, due to the flow of the second fluid to the main flow passage, air from the confluence flow passage and a portion of the second fluid is fed into the second branched flow passage by feeding the second fluid to the confluence portion passage, placing the first fluid and second fluid into contact in the main flow passage, and reducing air in the first fluid and the second fluid in the main flow passage.

16. The liquid feeding device according to claim 6, wherein the liquid feeding mechanism is further configured to move the first fluid and the second fluid between the third branched flow passage and the fourth branched flow passage multiple times to mix the first fluid and the second fluid.

17. The liquid feeding device according to claim 16, wherein the liquid feeding mechanism is further configured to feed, to a container on a downstream side of the fourth branch portion:
the mixed first and second fluids from the third flow passage and/or the fourth flow passage, and
a portion of the mixed first and second fluids located in the main flow passage downstream of the third branch portion.

18. The liquid feeding device according to claim 4, wherein:
- the liquid feeding mechanism has a control valve to feed the fluid by introducing or discharging air through opening and closing operations on at least one of the upstream side or the downstream side, and
- the liquid feeding mechanism is configured to close the control valve based at least in part on at least one of:
  - passage of a predetermined amount of time since opening the control valve; or
  - a change in air pressure of the air exceeding a threshold.

19. The liquid feeding device according to claim 18, wherein the liquid feeding mechanism comprises a pressure sensor to send a signal to indicate that the change in the air pressure exceeds the threshold.

\* \* \* \* \*